(12) United States Patent
Gregersen et al.

(10) Patent No.: US 11,377,408 B2
(45) Date of Patent: Jul. 5, 2022

(54) FIRE RETARDANT COMPOUNDS

(71) Applicant: The Boeing Company, Chicago, IL (US)

(72) Inventors: Kimberly-Alice D. Gregersen, Seattle, WA (US); James Craig Moreland, Kent, WA (US); Ekaterina A. Badaeva, Bellevue, WA (US); Andrew M. Zweig, Ellisville, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/596,437

(22) Filed: Oct. 8, 2019

(65) Prior Publication Data

US 2020/0031746 A1 Jan. 30, 2020

Related U.S. Application Data

(62) Division of application No. 16/126,746, filed on Sep. 10, 2018, now Pat. No. 10,479,747, which is a division of application No. 14/753,760, filed on Jun. 29, 2015, now Pat. No. 10,093,601.

(51) Int. Cl.
| | |
|---|---|
| *C07C 21/18* | (2006.01) |
| *C07C 21/14* | (2006.01) |
| *C07C 21/17* | (2006.01) |
| *C07C 21/02* | (2006.01) |
| *C07C 21/04* | (2006.01) |
| *A62C 99/00* | (2010.01) |
| *C09K 21/08* | (2006.01) |
| *A62C 3/08* | (2006.01) |
| *A62D 1/00* | (2006.01) |

(52) U.S. Cl.
CPC ............... *C07C 21/18* (2013.01); *A62C 3/08* (2013.01); *A62C 99/0018* (2013.01); *A62D 1/00* (2013.01); *A62D 1/0028* (2013.01); *C07C 21/02* (2013.01); *C07C 21/14* (2013.01); *C07C 21/17* (2013.01); *C09K 21/08* (2013.01); *C07C 21/04* (2013.01)

(58) Field of Classification Search
None
See application file for complete search history.

(56) References Cited

U.S. PATENT DOCUMENTS

| | | | |
|---|---|---|---|
| 3,709,948 A | 1/1973 | Haszeldine et al. | |
| 5,759,430 A | 6/1998 | Tapscott et al. | |
| 7,659,434 B2 | 2/2010 | Mukhopadhyay et al. | |
| 8,609,907 B2* | 12/2013 | Eicher .................... | C07C 17/25 570/156 |
| 8,820,079 B2 | 9/2014 | Zyhowski et al. | |
| 2001/0032960 A1 | 10/2001 | Grzyll et al. | |
| 2003/0060670 A1 | 3/2003 | Nair | |
| 2004/0144949 A1 | 7/2004 | Grigg | |
| 2006/0266976 A1 | 11/2006 | Minor et al. | |
| 2007/0096051 A1* | 5/2007 | Nappa ................... | A62D 1/0057 252/2 |
| 2007/0152200 A1 | 7/2007 | Hedrick et al. | |
| 2008/0292564 A1* | 11/2008 | Singh ....................... | C09K 3/30 424/47 |
| 2009/0302285 A1 | 12/2009 | Singh et al. | |
| 2010/0139274 A1 | 6/2010 | Zyhowski | |
| 2011/0009678 A1 | 1/2011 | Bonnet et al. | |
| 2013/0146316 A1 | 6/2013 | Griffith | |
| 2013/0280178 A1* | 10/2013 | Mueller ................. | A61K 8/046 424/47 |
| 2016/0178254 A1 | 6/2016 | Nishiguchi | |

FOREIGN PATENT DOCUMENTS

| | | | | |
|---|---|---|---|---|
| CN | 101300048 | | 11/2008 | |
| EP | 0252766 | | 1/1998 | |
| GB | 505573 | A * | 5/1939 | ........... C07C 17/358 |
| GB | 1285335 | | 8/1972 | |
| GB | 2370768 | | 7/2002 | |
| JP | 2009-513310 | | 4/2009 | |
| WO | 2007/059468 | | 5/2007 | |
| WO | 2007053737 | | 10/2007 | |
| WO | WO-2014028697 | A1 * | 2/2014 | ............... C09K 3/30 |
| WO | 2014/160609 | | 10/2014 | |

(Continued)

OTHER PUBLICATIONS

Petrov, V. A. et al. "Reaction of unsaturated polyhalo compounds with vanadium pentafluoride" Zhurnal Organicheskoi Khimii (1987), 23(1), 43-8; Abstract only (Year: 1987).*

Haszeldine, R. N. et al. "Addition of free radicals to unsaturated systems IX. The direction of free radical addition to allene and allyl chloride" Journal of the Chemical Society (1954), 2040-2 (Year: 1954).*

Henne, A. L. et al. "Perfluorinated olefins" American Chemical Society (1948), 70, 130-2 (Year: 1948).*

Fainberg, A. H. et al. "Molar Refractivity in Fluorine-Containing Perhalo Compounds" J. Org. Chem. 1965, 30, 3, 864-876 (Year: 1965).*

Teinz, K. et al. "Highly selective metal fluoride catalysts for the dehydrohalogenation of 3-chloro-1,1,1,3-tetrafluorobutane" Journal of Catalysis 282 (2011) 175-182 (Year: 2011).*

Apollo Scientific "2-Bromo-1,1,4,4,4-pentafluoro-1-butene" Published Dec. 27, 2010 (Year: 2010).*

(Continued)

*Primary Examiner* — Medhanit W Bahta
(74) *Attorney, Agent, or Firm* — McDonnell Boehnen Hulbert & Berghoff LLP

(57) ABSTRACT

Compounds with fire extinguishing properties having the formula:

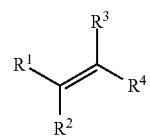

wherein $R^1$ is $-CR^5R^6R^7$ or $-CR^5R^6CR^8R^9R^{10}$ as well as fire extinguishing units including one or more of the compounds.

20 Claims, No Drawings

(56) References Cited

FOREIGN PATENT DOCUMENTS

| WO | WO-2014160910 A1 | * | 10/2014 | ............ | C09K 13/00 |
| WO | 2015/022958 | | 2/2015 | | |

OTHER PUBLICATIONS

McLinden, M. O. et al. "A thermodynamic analysis of refrigerants: Possibilities and tradeoffs for Low-GWP refrigerants5" International Journal of Refrigeration vol. 38, Feb. 2014, pp. 80-92 (Year: 2014).*

Tarrant, P. et al. J. Am. Chem. Soc. 1995, 77, pp. 3640-3642 (Year: 1995).*

Shmatov, Y. et al. "Electrophilic addition of halogens and hydrogen halides to a-halovinylacetylenes" 1976, Abstract Only pp. 1-2 (Year: 1976).*

Farrell, J. K. et al. "The Dehalogenation of α,β-Dibromo Acids. II. The Influence of the Acid Structure on the Yields of Bromoolefins" Journal of the American Chemical Society (1935), 57, 1281-3 (Year: 1935).*

Van Der Puy, M. "1,3-Dichloro-4,4,4-trifluorobut-2-ene as a 4-carbon building block containing a trifluoromethyl group" Journal of Fluorine Chemistry81 (1997) 187-191 (Year: 1997).*

Bissell (J. Org. Chem. 1962, 27, 4, 1482-1483) (Year: 1962).*

Roedig, A. et al. "Diacetylene from polychloro derivatives of the butane series" Justus Liebigs Annalen der Chemie (1953), 580, 20-4; Abstract only (Year: 1953).*

Hurd, C. D. et al. "Synthesis and Pyrolysis of Methylallene and Ethylacetylene" J. Am. Chem. Soc. 1931, 53, 1, 289-300 (Year: 1931).*

SynQuest Laboratories "1,2-dibromo-3,3,4,4,4-pentafluorobut-1-ene" Published 2013, pp. 1-2 (Year: 2013).*

ApolloScientific "1,2-dibromo-3,3,4,4,4-pentafluorobut-1-ene" Published Jul. 2014 (Year: 2014).*

Riches, J. et al. "A screening tool for Halon alternatives based on the flame ionisation detector" Fire Safety Journal 37 (2002) pp. 287-301.

Buchner, et al. "Reactions of Gaseous, Halogenated Propene Radical Cations with Ammonia: A Study of the Mechanism by Fourier Transform Ion Cyclotron Resonance" Chem. Eur. J. (1998) vol. 4, pp. 1799-1809.

Morken, et al., "Convenient Preparation and Functionalization of 2-Metallated Pentafluoropropenes", Tetrahedron Letters, 23:4271-4274 (1991).

Lu et al., "A Facile Route to Tetrafluoroallene" Journal of Fluorine Chemistry 75 (1995), pp. 83-86.

Morken et al., "Preparation of β,β-Difluoro-a-(trifluoromethyl) styrenes by Palladium-Catalyzed Coupling of Aryl Iodides with Pentafluoropropen-2-ylzinc Reagent" J. Org. Chem. (1993), pp. 1167-1172.

European Search Report prepared by the European Patent Office in application serial No. 16165477, dated Oct. 24, 2016.

Banks, RE. et al "Polyhalogenoallenes. Part VIII. 1 Routes to Tetrafluoroallene and Tetrafluoropropyne" Journal of the Chemical Society [Section] C: Organic (1969) vol. 7, pp. 1104-1107.

Bardin, Vadim V. et al. "Reactions of Perfluorinated Alkenyl-, Alkynyl-, Alkyltrifluoroborates, and Selected Hydrocarbon Analogues with the Halogenating Agents Hal2 {Hal=F, Cl, Br), "BrF" (BrF3-Br2 1: 1 ). and ICI" Zeitschrift uer Anorganische und Allgemeine Chemie (2012) vol. 638(3-4), pp. 565-579.

Banks, RE. et al. "Polyhalogeno-Allenes and -Acetylenes. Part XII[1] Further Studies on Routes To Tetrafluoroallen and Tetrafluoropropyne" Journal of Fluorine Chemistry (1977) vol. 10(6), pp. 487-493.

Bardin, Vadim V. et al. "Reactions of fluoroalk-1-en-1-yltrifluoroborate and perfluoroalk-1-yn-1-yltrifluoroborate salts and selected hydrocarbon analogues with hydrogen fluoride and with halogenating agents in aHF and in basic solvents" Journal of Fluorine Chemistry (2012) vol. 135, pp. 114-128.

Banks, RE. et al. "Perfluoro (Methylacetylene)" Tetrahedron Letters (1968) vol. 36, pp. 3909-3910.

Shchekotikhin, A.M. et al. Fluoro derivatives of acetylenic hydrocarbons. a-Fluorinated perhalopropynes Zhurnal Vsesoyuznogo Khimicheskogo Obshchestva im. D. L Mendeleeva (1962) vol. 7, pp. 580-582 (abstract).

MolPort (from Pubchem, Available date Jun. 21, 2011, pp. 1-6).

Tarrant, Paul et al. "The Peroxide-Initiated Addition of Some Polyfluorochloro-and Polyfluorobromoalkanes to Some Hydrocarbon Olefins", Journal of Organic Chemistry (1969) vol. 34(4), pp. 864.869.

Hals, Lyle J., et al., "The Preparation of Terminally Unsaturated Perfluoro Olefins by the Decomposition of the Salts of Perfluoro Acids", Journal of the American Chemical Society (1951), p. 4054.

Martinez, Henry et al. "Impact of fluorine substituents on the rates of nucleophilic aliphatic substitution and 13-elimination", Journal of Fluorine Chemistry (2011) vol. 135, pp. 167-175.

Office Action issued by the European Patent Office in application No. 16 165 477.7 dated Jan. 29, 2019.

PubChem; Available date Apr. 14, 2013, pp. 1-5.

Chinese Patent Application No. 2016-10220536.3, First Notification of Office Action, dated Jun. 2, 2020.

Japanese Patent Application No. 2016-126249, Notice of Reasons for Rejection, dated Jun. 22, 2020.

Notice of Reasons for Rejection issued by the Japanese Patent Office in application No. 2016-126249 dated Feb. 24, 2021.

Decision for Rejection issued by the Chinese Patent Office in application No. 201610220536.3 dated Feb. 20, 2021.

* cited by examiner

FIRE RETARDANT COMPOUNDS

CROSS REFERENCE TO RELATED APPLICATIONS

This application is a divisional of U.S. application Ser. No. 16/126,746, filed Sep. 10, 2018, which is a divisional of U.S. application Ser. No. 14/753,760, filed Jun. 29, 2015, the disclosure of each of which is incorporated herein by reference in its entirety.

BACKGROUND OF THE INVENTION

Field of the Invention

This invention concerns novel halogen containing compounds and fire extinguishing units including one or more fire extinguishing compounds.

Description of the Art

Halon 1301 is the predominant fire extinguishing agent used on aircraft. Halon 1301 is currently a banned substance with few exceptions. One such exception is its use as an aircraft fire extinguishing agent. However, even with this exception, new fire extinguishing compounds are needed because Halon 1301, as a banned substance, is no longer manufactured and eventually the current supply will be depleted. There is a need, therefore, for new fire extinguishing compounds and fire extinguishing units that contain them.

SUMMARY OF THE INVENTION

A first aspect of this invention is new compounds with fire extinguishing properties having the formula:

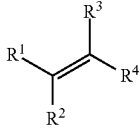

wherein $R^1$ is $-CR^5R^6R^7$ or $-CR^5R^6CR^8R^9R^{10}$;

$R^2$, $R^3$ and $R^4$ are each independently selected from halogen and hydrogen; and $R^5$, $R^6$, $R^7$, $R^8$, $R^9$ and $R^{10}$ are each independently selected from halogen and hydrogen, wherein at least one of $R^5$, $R^6$, $R^7$, $R^8$, $R^9$ and $R^{10}$ is halogen;

wherein when $R^1$ is $-CR^5R^6CR^8R^9R^{10}$ and $R^8$, $R^9$ and $R^{10}$ are each F, then at least one of $R^2$, $R^3$ and $R^4$ is halogen;

wherein when $R^1$ is $-CR^5R^6CR^8R^9R^{10}$ and $R^8$, $R^9$ and $R^{10}$ are each F and when $R^2$ is Br then one of $R^3$ and $R^4$ is halogen, or one of $R^5$ and $R^6$ is hydrogen;

wherein when $R^1$ is $-CR^5R^6R^7$ and $R^5$, $R^6$, $R^7$ are each F and $R^2$ is Br, then $R^3$ is halogen when $R^4$ is selected from hydrogen or Br, or $R^3$ is selected from hydrogen, Cl, Br or I when $R^4$ is F; and wherein when $R^1$ is $-CR^5R^6R^7$ and $R^5$, $R^6$, $R^7$ are each F and $R^2$ is I, then $R^3$ is halogen when $R^4$ is hydrogen, or $R^3$ is selected from hydrogen, F, Cl and I when $R^4$ is F.

In the above compounds: two or more substituents selected from $R^2$, $R^3$ and $R^4$ may be halogen; $R^2$, $R^3$ and $R^4$ may each be halogen; and/or $R^2$, $R^3$ and $R^4$ may each be independently selected from hydrogen, Br, Cl and I.

In the above compounds, $R^1$ may be $-CR^5R^6R^7$ in which case $R^5$, $R^6$ and $R^7$ may each be halogen or $R^5$, $R^6$, and $R^7$ may each be F.

In the above compounds, $R^1$ may be $-CR^5R^6CR^8R^9R^{10}$ in which case $R^8$, $R^9$ and $R^{10}$ may each be halogen; or $R^8$, $R^9$, and $R^{10}$ may each be F.

In the above compounds, $R^1$ may be $-CR^5R^6CR^8R^9R^{10}$ in which case $R^5$ and $R^6$ may each be halogen; or $R^5$ and $R^6$ may each be F.

In another aspect, the above compound may be 2-iodoperfluoro-1-butene; 2,3-dibromo-4,4,4-trifluoro-1-butene; 2-iodoperfluoro-1-butene; 2-bromoperfluoro-1-butene; 3-iodo-3,4,4,4-tetrafluoro-1-butene; 1-iodo-4,4,4-trifluoro-1-butene; 2-bromo-3,3,4,4,4-pentafluoro-1-butene; 1-bromo-4,4,4-trifluoro-1-butene; 2-chloro-3,3,4,4,4-pentafluoro-1-butene; and isomers thereof.

Yet another aspect of this invention are fire extinguishing units comprising a container and delivery system, the container containing at least one fire extinguishing compound having the formula:

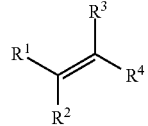

wherein $R^1$ is $-CR^5R^6R^7$ or $-CR^5R^6CR^8R^9R^{10}$;

$R^2$, $R^3$ and $R^4$ are each independently selected from halogen or hydrogen wherein at least one of $R^2$, $R^3$ and $R^4$ must be halo; and $R^5$, $R^6$, $R^7$, $R^8$, $R^9$ and $R^{10}$ are each independently selected from halogen or hydrogen wherein at least one of $R^5$, $R^6$, $R^7$, $R^8$, $R^9$ and $R^{10}$ must be halogen;

wherein when $R^1$ is $-CR^5R^6CR^8R^9R^{10}$ and $R^8$, $R^9$ and $R^{10}$ are each F, then at least one of $R^3$ and $R^4$ is halogen when $R^2$ is hydrogen, or $R^2$ is Cl, F or I when $R^3$ and $R^4$ are both hydrogen; and wherein when $R^1$ is $-CR^5R^6R^7$ and $R^5$, $R^6$, $R^7$ are each F then $R^2$, $R^3$ and $R^4$ are each hydrogen or halogen, or when $R^2$ is Br then $R^3$ is selected from halogen and $R^4$ is selected from hydrogen, Cl, F and I.

In the above fire extinguishing unit, the fire extinguishing compound may include substituents $R^2$, $R^3$ and $R^4$ wherein two or more of the substituents are halogen; or where each substituent is halogen; or where each substituent is selected from hydrogen, Br, Cl and I.

In the above fire extinguishing unit, the fire extinguishing compound includes substituent $R^1$ that may be $-CR^5R^6R^7$ in which case $R^5$, $R^6$, and $R^7$ may each be halogen; or $R^5$, $R^6$, and $R^7$ may each be F.

In the above fire extinguishing unit, the fire extinguishing compound includes substituent $R^1$ that may be $-CR^5R^6CR^8R^9R^{10}$ in which case $R^8$, $R^9$, and $R^{10}$ may each be halogen; or $R^8$, $R^9$, and $R^{19}$ may each be F; or in which case $R^5$ and $R^6$ may each be halogen or may each be F.

In the above fire extinguishing unit, the fire extinguishing compound may be selected from 2-iodoperfluoro-1-butene; 2,3-dibromo-4,4,4-trifluoro-1-butene; 2-iodoperfluoro-1-butene; 2-bromoperfluoro-1-butene; 3-iodo-3,4,4,4-tetrafluoro-1-butene; 1-iodo-4,4,4-trifluoro-1-butene; 2-bromo-3,3,4,4,4-pentafluoro-1-butene; 1-bromo-4,4,4-trifluoro-1-butene; 2-chloro-3,3,4,4,4-pentafluoro-1-butene; 2-bromo-1,1,3,3,3-pentafluoropropene; 2-iodo-1,1,3,3,3- pentafluoropropene; 2-iodo-3,3,3-trifluoropropene, isomers thereof and combinations thereof.

DESCRIPTION OF CURRENT EMBODIMENTS

The present invention relates to novel compounds that have fire retarding properties as well as fire extinguishing units that include one or more fire retarding compounds. The compounds discussed below are all expected to have acceptable to very good abilities to extinguish a heptane flame—Heptane Cap Burner Value.

Useful fire extinguishing compounds have the general formula:

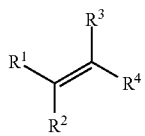

Formula I wherein $R^1$ is —$CR^5R^6R^7$ or —$CR^5R^6CR^8R^9R^{10}$;

$R^2$, $R^3$ and $R^4$ are each independently selected from halogen or hydrogen wherein at least one of $R^2$, $R^3$ and $R^4$ must be halo; and $R^5$, $R^6$, $R^7$, $R^8$, $R^9$ and $R^{10}$ are each independently selected from halogen or hydrogen wherein at least one of $R^5$, $R^6$, $R^7$, $R^8$, $R^9$ and $R^{10}$ must be halogen;

wherein when $R^1$ is —$CR^5R^6CR^8R^9R^{10}$ and $R^8$, $R^9$ and $R^{10}$ are each F, then at least one of $R^3$ and $R^4$ is halogen when $R^2$ is hydrogen, or $R^2$ is Cl, F or I when $R^3$ and $R^4$ are both hydrogen; and wherein when $R^1$ is —$CR^5R^6R^7$ and $R^5$, $R^6$, $R^7$ are each F then $R^2$, $R^3$ and $R^4$ are each hydrogen or halogen, or when $R^2$ is Br then $R^3$ is selected from halogen and $R^4$ is selected from hydrogen, Cl, F and I.

In this aspect, when $R^1$ is —$CR^5R^6R^7$ or —$CR^5R^6CR^8R^9R^{10}$ then two or more substituents selected from $R^2$, $R^3$ and $R^4$ may be halogen; or $R^2$, $R^3$ and $R^4$ may each be halogen; or $R^2$, $R^3$ and $R^4$ may each be independently selected from hydrogen, Br, Cl and I.

Alternatively, in this aspect, when $R^1$ is —$CR^5R^6R^7$ then $R^5$, $R^6$, and $R^7$ may each be halogen and more narrowly $R^5$, $R^6$, and $R^7$ may each be F. Moreover, when $R^1$ is —$CR^5R^6R^7$ then the fire extinguishing compound of this invention may be selected from 2-bromo-1,1,3,3,3-pentafluoropropene; 2-iodo-1,1,3,3,3-pentafluoropropene; 2-iodo-3,3,3-trifluoropropene and combinations thereof identified in Table 1 below.

In the aspect above, when $R^1$ is —$CR^5R^6CR^8R^9R^{10}$ then $R^8$, $R^9$, and $R^{10}$ may each be halogen and more narrowly, $R^8$, $R^9$, and $R^{10}$ may each be F. Alternatively or in addition, when $R^1$ is —$CR^5R^6CR^8R^9R^{10}$ then $R^5$ and $R^6$ may each be halogen and more narrowly $R^5$ and $R^6$ may each be F. Finally, when $R^1$ is —$CR^5R^6CR^8R^9R^{10}$ then the fire extinguishing compound of this invention may be selected from 2-iodoperfluoro-1-butene; 2,3-dibromo-4,4,4-trifluoro-1-butene; 2-iodoperfluoro-1-butene; 2-bromoperfluoro-1-butene; 3-iodo-3,4,4,4-tetrafluoro-1-butene; 1-iodo-4,4,4-trifluoro-1-butene; 2-bromo-3,3,4,4,4-pentafluorobutene; 2-chloro-3,3,4,4,4-pentafluoro-1-butene; isomers thereof and combinations thereof as identified in Table 1 below.

TABLE 1

| Compound Name | Formula |
|---|---|
| 2-bromo-1,1,3,3,3-pentafluoropropene | |
| 2-iodo-1,1,3,3,3-pentafluoropropene | |
| 2-iodo-3,3,3-trifluoropropene | |
| 1-bromo-4,4,4-trifluoro-1-butene | |
| 2,3-dibromo-4,4,4-trifluoro-1-butene | |
| 2-iodoperfluoro-1-butene | |
| 2-bromoperfluoro-1-butene | |
| 3-iodo-3,4,4,4-tetrafluoro-1-butene | |
| 1-iodo-4,4,4-trifluoro-1-butene | |
| 2-bromo-3,3,4,4,4-pentafluorobutene | |
| 2-chloro-3,3,4,4,4-pentafluoro-1-butene | |

In an alternative aspect, the fire extinguishing compounds have the general Formula I above wherein $R^1$ is —$CR^5R^6R^7$ or —$CR^5R^6CR^8R^9R^{10}$;

$R^2$, $R^3$ and $R^4$ are each independently selected from halogen and hydrogen; and $R^5$, $R^6$, $R^7$, $R^8$, $R^9$ and $R^{10}$ are each independently selected from halogen and hydrogen, wherein at least one of $R^5$, $R^6$, $R^7$, $R^8$, $R^9$ and $R^{10}$ is halogen, and wherein when $R^1$ is —$CR^5R^6CR^8R^9R^{10}$ and $R^8$, $R^9$ and $R^{10}$ are each F, then at least one of $R^2$, $R^3$ and $R^4$ is halogen;

wherein when $R^1$ is —$CR^5R^6CR^8R^9R^{10}$ and $R^8$, $R^9$ and $R^{10}$ are each F and when $R^2$ is Br then one of $R^3$ and $R^4$ is halogen, or one of $R^5$ and $R^6$ is hydrogen;

wherein when $R^1$ is —$CR^5R^6R^7$ and $R^5$, $R^6$, $R^7$ are each F and $R^2$ is Br, then $R^3$ is halogen when $R^4$ is selected from hydrogen or Br, or $R^3$ is selected from hydrogen, Cl, Br or I when $R^4$ is F; and wherein when $R^1$ is —$CR^5R^6R^7$ and $R^5$, $R^6$, $R^7$ are each F and $R^2$ is I, then $R^3$ is halogen when $R^4$ is hydrogen, or $R^3$ is selected from hydrogen, F, Cl and I when $R^4$ is F.

In this alternative aspect, when $R^1$ is —$CR^5R^6R^7$ or —$CR^5R^6CR^8R^9R^{10}$ then $R^2$, $R^3$ and $R^4$ may each be halogen or $R^2$, $R^3$ and $R^4$ may each be independently selected from hydrogen, Br, Cl and I. In another alternative, when $R^1$ is —$CR^5R^6R^7$ then $R^5$, $R^6$, and $R^7$ may each be halogen or $R^5$, $R^6$, and $R^7$ may each be F.

Also in this alternative aspect, when $R^1$ is —$CR^5R^6CR^8R^9R^{10}$ then $R^8$, $R^9$, and $R^{10}$ may each be halogen or more narrowly $R^8$, $R^9$, and $R^{10}$ may each be F. Moreover, when $R^1$ is —$CR^5R^6CR^8R^9R^{10}$ then $R^5$ and $R^6$ may each be halogen and more narrowly $R^5$ and $R^6$ may each be F.

Further in this alternative aspect, the compound is selected from 2-iodo perfluoro-1-butene; 2,3-dibromo-4,4,4-trifluoro-1-butene; 2-bromoperfluoro-1-butene; 3-iodo-3,4,4,4-tetrafluoro-1-butene; 1-iodo-4,4,4-trifluoro-1-butene; 2-bromo-3,3,4,4,4-pentafluorobutene; 1-bromo-4,4,4-trifluoro-1-butene; 2-chloro-3,3,4,4,4-pentafluoro-1-butene; and isomers thereof as identified in Table 1 above.

As used herein the term halogen is used in its normal and customary manner to refer to chloro (Cl), fluoro (F), bromo (Br) and iodo (I).

The fire extinguishing compounds identified above are useful alone or combined with other fire extinguishing composition ingredients when used in a fire extinguishing unit to suppress or extinguish fires. Fire suppression refers to a use of agents such as gases, liquids, solids, chemicals and mixtures thereof to extinguish combustion.

The fire extinguishing compounds discussed above are useful in fire extinguishing units that include various containers and delivery systems that may in turn be used in a variety of fire extinguishing applications. Such units and delivery systems include, but are not limited to hand-held fire extinguishing units, permanent fire extinguishing systems, modular fire extinguishing systems and the like which may be used in the home, computer rooms, kitchens, factories warehouse facilities, airplanes, cars, trucks, heavy-equipment, etc. The fire extinguishing compound(s) may be used in units that are used in flood and streaming-type fire extinguishing applications. The compounds may be placed in any known container that is used to hold fire extinguishing compounds and compositions such as hand-held extinguishing containers, tanker trucks such as those associated with fire trucks, wheeled containers and the like.

Some fire suppression units or systems use a "total flooding" or a "non-total flooding" methods to apply an extinguishing agent in an enclosed volume. The total flooding or the non-total flooding method may achieve a concentration of the extinguishing agent as a volume percent to air of the extinguishing agent sufficient to suppress or extinguish a fire.

In aircraft applications, each cargo compartment may have its own dedicated distribution system comprising tubes routed to nozzles in a cargo bay. The nozzles may be mounted in pans down a centerline of a cargo bay ceiling liner. An extinguishing agent including one or more of the fire extinguishing compounds disclosed above may also be released directly into a compartment where there are no tubes or nozzles, as the agent container(s) is/are plugged directly into the compartment. Fire suppression systems may be operated automatically by an automatic detection and control mechanism, and/or manually by manual activation of an actuator via a local and/or remote switch, a combination thereof, and the like.

Fire suppression units and delivery systems are generally sized for worst case scenarios that may occur during descent when an aircraft begins to re-pressurize. Therefore, additional equipment and suppressant chemicals required during descent may determine a size of an overall system with resulting added weight and volume.

The useful fire extinguishing units include one or more of the above fire extinguishing compounds and optionally include additional active and inert fire suppression or extinguishing ingredients, Active ingredients might include, for example, oxygen depleting agents, heat removing (endothermic) agents such as carbon dioxide, additional flame retarding or extinguishing agents and the like.

Fire suppression units, delivery systems and methods that can employ one or more fire extinguishing compounds of this invention are well known. For example, U.S. Pat. No. 8,925,642 discloses a scalable cargo fire suppression agent distribution system. The system includes a plurality of fire suppression agent supply source units. During use, a supply source unit subset of the total source units is/are selected based on an operation condition, and a fire suppression agent from the supply source unit subset is distributed during the operation condition. In this manner, significantly less storage space and supply source container weight is required to store fire suppression agents.

In another example, U.S. Pat. No. 7,510,022 is directed to fire suppression systems for aircraft cargo compartments. The fire suppression systems can include at least one fire-suppressant vessel, at least one discharge conduit coupled to the at least one fire-suppressant vessel, and a valve arrangement coupled to the fire-suppressant vessel and the discharge conduit. The valve arrangement has multiple settings that allows for the control of the discharge rate of a fire suppressant held in the vessels.

In yet another example, U.S. Pat. No. 4,726,426 discloses a fire suppression system for extinguishing fires in an aircraft passenger cabin. The system uses the passenger cabin environmental control system ductwork to direct a fire suppression agent from a vessel or container in the cargo hold into the passenger cabin. Other examples of fire suppression systems are within the knowledge of one skilled in the art.

Example—Compound Synthesis Methods

Fire retardant compounds of this invention can be prepared by the synthesis methods detailed in this example. Moreover, the skilled person would understand that there are other synthesis methods that can be used to prepare the fire retardant compounds identified above.

Method A

These synthesis procedures use a ($C_3HF_5O$) aldehyde that is prepared by esterifying pentafluoropropionic acid with methanol and trace amount of sulfuric acid. The ester, methyl pentafluoropropionate, is purified by distillation. Next, the methyl pentafluoropropionate is reduced to 2,2,3,3,3-pentafluoropropionaldehyde ($C_3HF_5O$) with a slight excess of di-isobutylaluminum hydride and purified by distillation.

(1) 2-iodoheptafluorobutene and 2-bromoheptafluorobutene are synthesized using the ($C_3HF_5O$) aldehyde made above as follows:
  (a) Perform a one-pot reaction using one equivalent of the ($C_3HF_5O$) aldehyde, three equivalents of (chlorodifluoromethyl)trimethyl silane and three equivalents of triphenylphosphine in Tetrahydrofuran ("THF") at 70° C. for 10 hours. The "$CF_2$" equivalent converts the R(H)C=O from the aldehyde to an R(H)C=$CF_2$ and the product is purified by distillation.
    i. 2-iodoheptafluorobutene is derived by abstracting aldehyde hydrogen with one equivalent of n-butyl lithium in THF at −78° C., warm, and quenching with iodine.
    ii. 2-bromoheptafluorobutene is derived by abstracting aldehyde hydrogen with one equivalent of n-butyl lithium in THF at −78° C., warm, and quenching with bromine.
(2) 2-Chloro-3,3,4,4,4-pentafluorobutene is synthesized using the ($C_3HF_5O$) aldehyde made above as follows:
  a. Perform a one-pot reaction using one equivalent of the ($C_3HF_5O$) aldehyde, three equivalents of (chloromethyl)trimethyl silane and three equivalents of triphenylphosphine in THF at 70° C. for 10 hours. The "$CH_2$" equivalent converts the R(H)C=O from the aldehyde to an alkene, e.g. R(H)C=$CH_2$. The resulting product is 3,3,4,4,4-pentafluoro-1-butene and it is purified by distillation.
  b. 2-Chloro-3,3,4,4,4-pentafluorobutene is derived by abstracting aldehyde hydrogen with one equivalent of n-butyl lithium in THE at −78° C., warming and then quenching with aqueous chlorine.

Method B

1-Iodo-4,4,4-trifluoro-1-butene and 1-bromo-4,4,4-trifluoro-1-butene are synthesized as follows:

React propargyl chloride with one equivalent of tris (triphenylphosphine)copper trifluoromethane, $(Ph_3P)_3CuCF_3$ to give 4,4,4-trifluoro-1-butyne. Next, react 4,4,4-trifluoro-1-butyne with dibutylaluminum hydride in n-heptane solution at <40° C.) and then warm the solution to 50° C.

a. 1-Iodo-4,4,4-trifluorobutene is derived from the reaction product above by cooling the solution to −50° C., and quenching with iodine to give a mixture of cis- and trans-1-iodo-4,4,4-trifluoro-1-butene.
  1-Bromo-4,4,4-trifluoro-1-butene is derived from the reaction product above by using bromine instead of iodine in reaction step (a) above to form a cold quench mixture of cis- and trans-1-bromo-4,4,4-trifluoro-1-butene.

Method C 2,3-dibromo-4,4,4-trifluoro-1-butene is prepared by reacting 2-bromo-4,4,4-trifluoro-1-butene with one equivalent of sodium t-butoxide in t-butanol at low temperature (−78° C. to −40° C.) and then quenching the solution slowly with bromine to yield the above-mentioned dibromo product.

2-bromo-4,4,4-trifluoro-1-butene is prepared by reacting 2,3-dibromo-1-propene with one equivalent of (1,10-phenanthroline)(trifluoromethyl) copper Method D 3,4,4,4-tetrafluoro-1-butene is prepared by reacting 3-bromo-3-fluoro-1-propene with (1,10-phenanthroline)(trifluoromethyl) copper(I).

3,4,4,4-tetrafluoro-3-iodo-1-butene is prepared by reacting sodium t-butoxide with 3,4,4,4-tetrafluoro-1-butene, followed by quenching with iodine.

The foregoing description of the specific embodiments will reveal the general nature of the disclosure so others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A compound which is dibromo-4,4,4-trifluoro-1-butene or 1-bromo-4,4,4-trifluoro-1-butene.
2. A compound of claim 1, wherein the compound is contained in a fire extinguishing unit.
3. A compound according to claim 2, wherein the fire extinguishing unit is a hand-held fire extinguishing unit.
4. A compound according to claim 2, wherein the fire extinguishing unit is a permanent fire extinguishing unit.
5. A compound according to claim 2, wherein the fire extinguishing unit is a modular fire extinguishing unit.
6. A compound according to claim 2, wherein the fire extinguishing unit is a component of an aircraft.
7. A compound according to claim 6, wherein the fire extinguishing unit further comprises at least one nozzle.
8. A compound according to claim 1, wherein the compound is contained in a fire extinguishing unit, the fire extinguishing unit is a component of an aircraft and further comprises at least one nozzle, and fire extinguishing unit additionally contains carbon dioxide.
9. A compound which is 2,3-dibromo-4,4,4-trifluoro-1-butene.
10. A compound of claim 9, wherein the compound is contained in a fire extinguishing unit.
11. A compound according to claim 10, wherein the fire extinguishing unit is a component of an aircraft.
12. A compound according to claim 11, wherein the fire extinguishing Unit further comprises at least one nozzle.
13. A compound according to claim 10, wherein the fire extinguishing unit contains at least one additional fire suppression or extinguishing agent selected from the group consisting of oxygen depleting agents, heat removing agents, flame retarding agents and flame extinguishing agents.
14. A compound according to claim 13, wherein the at least one additional fire suppression or extinguishing is carbon dioxide.
15. A compound which is 1-bromo-4,4,4-trifluoro-1-butene.
16. A compound of claim 15, wherein the compound is contained in a fire extinguishing unit.
17. A compound according to claim 16, wherein the fire extinguishing unit is a component of an aircraft.
18. A compound according to claim 17, wherein the fire extinguishing unit further comprises at least one nozzle.

19. A compound according to claim 16, wherein the fire extinguishing unit contains at least one additional fire suppression or extinguishing agent selected from the group consisting of oxygen depleting agents, heat removing agents, flame retarding agents and flame extinguishing agents.

20. A compound according to claim 19, wherein the at least one additional fire suppression or extinguishing is carbon dioxide.

\* \* \* \* \*